US00PP26057P3

(12) United States Plant Patent
Chaparro et al.

(10) Patent No.: US PP26,057 P3
(45) Date of Patent: Nov. 10, 2015

(54) PEACH TREE NAMED 'UFGEM'

(50) Latin Name: ***Prunus persica* (L.) Batsch**
Varietal Denomination: UFGem

(71) Applicant: Florida Foundation Seed Producers, Inc., Marianna, FL (US)

(72) Inventors: Jose X. Chaparro, Gainesville, FL (US); Wayne B. Sherman, New Smyrna Beach, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 179 days.

(21) Appl. No.: 13/987,608

(22) Filed: Aug. 13, 2013

(65) Prior Publication Data

US 2015/0052644 P1 Feb. 19, 2015

(51) Int. Cl.
*A01H 5/08* (2006.01)

(52) U.S. Cl.
USPC ..... Plt./197

CPC ..... *A01H 5/0868* (2013.01)

(58) Field of Classification Search
USPC ..... Plt./197
See application file for complete search history.

(56) References Cited

U.S. PATENT DOCUMENTS

| | | | |
|---|---|---|---|
| PP5,251 | P | 6/1984 | Doyle |
| PP14,764 | P2 | 5/2004 | Sherman |
| PP20,294 | P2 | 9/2009 | Chaparro |

*Primary Examiner* — June Hwu
(74) *Attorney, Agent, or Firm* — Dentons US LLP

(57) ABSTRACT

'UFGem' is a new and distinct variety of peach tree that has an estimated winter chilling requirement of 175 chill units. The tree is of large size and is highly vigorous with a semi-upright growth habit. Flowers are showy and pink and leaf glands are small and reniform. Trees are self-fertile and regularly bear heavy annual crops of early-season fruit, which are large for its ripening season. Fruit are firm, yellow, and non-melting, clingstone flesh. Fruit are uniform, substantially symmetrical in shape, attractive, and have a bright red skin over nearly 100% of the deep yellow ground color. The fruit usually ripens 5 to 7 days after 'UFSun' in early May in Gainesville, Fla.

1 Drawing Sheet

Latin name of the genus and species of the plant claimed: *Prunus persica* (L.) Batsch.

Variety denomination: 'UFGem'.

BACKGROUND OF THE INVENTION

The present invention relates to a new and distinct variety of peach (*Prunus persica* (L.) Batsch) tree named 'UFGem'. Particularly, the present invention relates to a peach tree that produces a high percentage of red skin with an attractive deep yellow ground color on the fruit. The fruit has good eating quality with clingstone and non-melting, yellow flesh. Fruit are mature for fresh market in early to mid-May in Gainesville, Fla. Fruit are produced on a tree adapted to a mild winter climate. Contrast is made to 'UFSun' peach (U.S. Plant Pat. No. 14,764) for reliable description. This new variety 'UFGem' is a promising candidate for commercial success in that it retains fruit firmness from its non-melting flesh at the full-flavor, tree-ripe stage for a week on the tree.

This peach tree (genotype) originated in a cultivated area of the fruit breeding program at the University of Florida, located in Gainesville, Fla. The seed parent was 'FlordaBest' (U.S. Plant Pat. No. 20,294). The pollen parent was AP99-20c peach, which resulted from a cross of Fla.94-40wc×'Springbaby' (unpatented). Fla.94-40wc resulted from a cross of 'Improved Diamante' (unpatented)×'Snowflame' (U.S. Plant Pat. No. 5,251). 'UFGem' was determined to have unique tree and fruit characteristics, making it worthy for commercial fresh fruit production. 'UFGem' peach tree was selected in 2006, and was designated and tested as Fla. 06-08c. It was asexually reproduced by budding on 'Flordaguard' (unpatented) seedling rootstock in Gainesville, Fla., where the selection was made and trees were also tested. Asexually propagated plants remained true to type. There are no known effects of this rootstock on this scion cultivar.

When compared with its parent varieties, 'UFGem' is a medium to large, yellow-fleshed peach with non-melting flesh. The fruit typically have from 90-100% blush on the peel. 'UFGem' requires approximately 175 chill hours below 45° F. to bloom and reaches full bloom around January 23 in Gainesville, Fla. Pollen parent AP99-20c is a medium to large peach having white, non-melting flesh. The fruit of AP99-20c typically have blush on 60-70% of the peel. AP99-20c requires approximately 350 chill hours below 45° F. to bloom, with bloom typically occurring around February 22 in Gainesville, Fla. Seed parent 'Flordabest' is a medium to large, yellow-fleshed peach with melting flesh. The fruit typically have from 90-100% blush on the peel. 'Flordabest' requires approximately 275 chill hours below 45° F. to bloom and reaches full bloom around February 9 in Gainesville, Fla.

'UFGem' differs from 'UFSun' by having fruit of a higher percentage of red skin and ripening one week later. 'UFGem' has larger fruit size and more red in the skin than 'UFSun'.

SUMMARY OF THE INVENTION

The new and distinct variety of peach tree bears yellow, non-melting flesh fruit with a high percentage of red skin. 'UFGem' peach tree blooms about 3 to 5 days after 'UFSun' peach in Gainesville, thus the estimated endodormancy requirement is 175 chill units. 'UFGem' peach tree is characterized by fruit of excellent flavor and eating quality. The trees are vigorous, productive, and without alternate bearing. Trees attained a height of 2.5 meters and a spread of 2 meters in 2 years in Gainesville. Terminal growth of up to 1 meter annually is common on mature 4-year-old trees with normal pruning to a vase shape. The first fruit ripen in early to mid-May in Gainesville, or in about 80 to 85 days from full bloom. The fruit are uniformly large for an early season peach. The skin on ripe fruit has near 100% red over a yellow ground color. There is no red pigment in the flesh at the pit. The flower anthers are light yellow, a common characteristic of many peach cultivars. Flower petals are pink and showy.

BRIEF DESCRIPTION OF THE DRAWINGS

The accompanying drawing is a color photograph that shows a typical specimen of the fruit, leaf, and stem of the new variety as nearly true as it is reasonably possible to make in a color illustration of this type.

FIG. 1—Shows an attractive shape and exterior coloration of six specimens of fruit above a ruler in a stem-end view, a blossom-end view, side views facing and perpendicular to the suture, and fruits cut longitudinally showing the flesh with and without a pit in place.

DETAILED BOTANICAL DESCRIPTION

The tree, flowers, and fruit may vary in slight detail due to variations in soil type, cultural practices, and climatic condition. The potential for commercial production of fresh fruit by peach tree 'UFGem' is high, due to its attractive red skin over a bright yellow ground color, with good flavor balance of sugar and acid, and exceptional firmness due to its non-melting flesh. The present botanical description is that of the variety as grown on 4-year-old trees on 'Flordaguard' rootstock under the ecological conditions prevailing in Gainesville, Fla. Variations of the usual magnitude to changes in climatic growing conditions, soils, fertilization, pruning, irrigation, and pest control are to be expected. Colors (except those in common terms) are described from "The Pantone Book of Color" published by H. N. Abrams, Inc., N.Y. 1990.

Phenotypic Description of *Prunus persica* (L.) Batsch 'UFGem'

Classification:

*Botanical.*—*Prunus persica* (L.) Batsch.

*Common name.*—Peach.

Parentage: 'UFGem' is a peach tree cross between seed parent 'FlordaBest' and pollen parent AP99-20c peach. AP99-20c resulted from a cross of Fla.94-40wc×'Springbaby'. Fla.94-40wc resulted from a cross of 'Improved Diamante'×'Snowflame'.

Tree:

*Size.*—Large, when trained to an open vase form.

*Tree growth* (*height*).—5-7 feet for the first growing season in the field; annual growth of 3-5 feet.

*Tree growth* (*spread*).—4-6 feet in the first growing season in the field.

*Vigor.*—Vigorous; must be pruned in the summer and winter to keep tree height restricted and to keep center of open vase form. Tree responds typically to irrigation and fertilization.

*Density.*—Light to medium in branching habit, but requires pruning to open the tree center to permit high sunlight entrance for enhancing interior flower bud set, fruit color, and sugar.

*Form.*—Semi-upright.

*Hardiness.*—Hardy with respect to typical north central Florida winters. Chill units for endodormancy are estimated at 175 chill units.

*Bearer.*—Annual and without alternate bearing, and must be fruit-thinned to avoid limb breakage and obtain large fruit size. Trees annually set several times the number of fruit for a desired crop load.

Trunk:

*Size.*—Large trunk, attaining 18-cm diameter at a height of 30 cm above the ground at the end of 4 years of growth.

*Texture.*—Medium smooth, but changes to medium shaggy as tree ages.

*Bark color.*—Variable with other bark colors; mostly gray, Flint Gray (Pantone 16-5803).

*Lenticels.*—Moderate number (18 per 4 square inches of surface area of the trunk), large (4-10 mm) with the center closed.

Branches:

*Size.*—Strong growth of scaffold branches. This is not distinctive of the variety.

*Texture.*—Relatively smooth, medium amount of lenticels attaining size found on trunk and old scaffolds. Roughness increases with age.

*Color.*—New wood is light green, Sweet Pea (Pantone 15-0531); Old wood is more brown, Copper Brown (Pantone 18-1336).

*Crotch angle.*—Angles selected at 50-80 degrees in the first year of tree training. Natural angles are within the normal range of standard varieties for a semi-upright tree.

Leaves:

*Size.*—Medium.

*Length.*—15-18 cm, including the petiole.

*Width.*—3.1-4.4 cm in mid-shoot on vigorous, upright summer growth.

*L/W ratio.*—Between 4.3 and 5.8.

*Thickness.*—Regular and average for peach varieties; not distinctive of the variety.

*Shape.*—Lanceolate with an acuminate tip.

*Base.*—Cuneate.

*Margin.*—Serrulate.

*Surface.*—Upper surface: Glabrous. Lower surface: Medium to large veins that are pinnately netted.

*Color.*—Upper surface: Slightly darker green than lower; Avocado (Pantone 18-0430). Lower surface: Green; Mosstone (Pantone 14-0525).

*Petiole.*—Length: Average 9.5 mm. Width: Average 2.0 mm diameter. Color: Light green, Sweet Pea (Pantone 15-031) on young full-sized leaves of spring.

*Leaf glands.*—Two to four leaf glands located at the distal end of the petiole at or near the base of the leaf blade. Glands are small (1 mm) and reniform in shape.

*Leaf gland color.*—Green Olive (Pantone 17-0535).

*Leaf stipules.*—Two stipules located at the proximal end of the petiole near the stem of young leaves. Stipules are approximately 10 mm long and Green Olive (Pantone 17-0535) in color.

*Leaf bud burst.*—Variable, depending on climatic conditions, ranging from 0 to 20 days from time of bloom.

Flowers and flower buds:

*Type.*—Showy, variable in size based on location and season, but within the range of commercial varieties.

*Diameter.*—Averaged 36 mm.

*Blooming period.*—3-5 days after 'UFSun' peach; average January 22-27 in Gainesville, occurring over a 7-10 day period, dependent on ambient temperature.

*Flower bud size.*—Length: Averages 2.5 mm in late summer.

*Flower bud shape.*—Plump, conic.

*Color.*—Brown, Copper Brown (Pantone 18-1336) in late summer.

*Fertility.*—Self-fertile.

*Flower petals.*—Number: 5. Length: 18 mm average. Width: 13 mm average. Shape: Obovate, edges vary from smooth to slightly undulate. Surface: Glabrous.

*Color.*—Pink, Almond Blossom (Pantone 13-2006). Margin: Smooth.

*Sepal.*—Number (per flower): 5. Lower surface: Pubescent.

*Calyx.*—Cup: Medium large (5 mm diameter at the top, and 5 mm depth).

*Pedicel.*—Number: 5. Length: 5-8 mm, not distinguishing for the variety.

*Stamen.*—Length: 9-16 mm. Number: 35-45.

*Anther.*—Color: Yellow, Golden Cream (Pantone 13-0939) at flower opening. Pollen: Abundant and light yellow, Lemon Drop (Pantone 12-0736).

*Pistil.*—Number: 1 per flower. Surface: Pubescent. Length: 15-17 mm, from tip of stigma to base of ovary. Color: Shape and color are within the range of standard commercial varieties; Light green, Celery Green (Pantone 12-0532). Ovary pubescence: Short pubescence typical for peaches.

*Floral nectary color.*—Typical of that observed in yellow-fleshed peaches.

*Blossom period.*—Average January 22-27 in Gainesville, Fla. over a 7-10 day period, depending on ambient temperature.

*Fragrance.*—Not noticeable as is normal for most peach varieties.

Fruit:

*Maturity when described.*—Tree ripe, Apr. 19, 2013 in Gainesville, Fla. Date of first picking: Apr. 19, 2013 in Gainesville. Date of last picking: Apr. 30, 2013 in Gainesville.

*Fruit drop.*—Little, if any, pre-harvest fruit drop observed.

*Size.*—Uniform, medium to large; large size for early season maturity at 140 to 160 g; Size varies with crop load, soil type, and availability of soil moisture.

*Diameter.*—63 mm average.

*Length.*—60 mm average.

*Longitudinal section form.*—Slightly squat.

*Transverse section through diameter.*—Round; apex is slightly recessed.

*Suture.*—Inconspicuous in color and slightly depressed.

*Pedicel.*—Length: 7-9 mm. Width: 3-4 mm. Color: Green, Endive (Pantone 13-0632).

*Ventral surface.*—Rounded.

*Apex.*—Slightly recessed.

*Crater at pedicel.*—Flaring circular; stem depressing on base of fruit. Crater depth is 6-10 mm, breadth is 22 mm at top, and 3 mm at pedicel attachment.

Skin:

*Tenacity.*—Tenacious to flesh.

*Thickness.*—Medium, not a distinguishable feature.

*Texture.*—Smooth and tender, similar to that of 'UFSun' peach.

*Color.*—Dark red, Baked Apple (Pantone 18-1648) to Raspberry Wine (Pantone 18-1741) over 90-100% of the skin at harvest.

*Ground color.*—Deep yellow, Sunset Gold (Pantone 13-0940).

*Pubescence.*—Short to medium; soft to touch.

*Flavor.*—No astringency observed.

Flesh:

*Ripening consistency.*—Consistently within each fruit, and in general throughout the tree.

*Fibers.*—Very fine, small, and tender throughout the flesh.

*Juice.*—Abundant.

*Color.*—Deep Yellow, Amber Yellow (Pantone 13-0942) with a small amount of red, Hot Coral (Pantone 17-1656) on the sun exposed side of the fruit, especially under dry, hot conditions. There is no red at the pit.

*Texture.*—Firm, fine, juicy, non-melting when fully ripe.

*Aroma.*—Moderate and in the middle range of commercial peach varieties.

*Eating quality.*—Excellent, sweet, and slightly acid; Titratable acidity was 0.88 as percent malic acid.

*Penetrometer firmness.*—1.4 kg on average, at harvest with a standard 8-mm tip.

*Sucrose content* (*average brix*).—Near 12.

*Oxidation* (*browning*).—Not noticeable on bruised fruit or in flesh of cut fruit upon several hours of exposure to air in tree ripe fruit beginning to soften.

*Amygdalin.*—Undetected.

Stone:

*Type.*—Clingstone; adhering to flesh even at softening.

*Shape.*—Elliptic with an acuminate tip and acute base.

*Sides.*—Near equal.

*Size.*—Medium to small. Length: 30 mm average. Average diameter at the equator perpendicular to the suture: 25 mm. Average thickness at the equator across (facing) the suture: 18 mm. Average wall thickness at the equator perpendicular to suture: 5-6 mm.

*Color.*—Light Brown, Beige (Pantone 14-1118).

*Outer surface.*—Furrowed along the ventral edge and lightly pitted from the apex toward the base.

*Ridges.*—2 ridges noticeable at the suture line from base to apex.

*Tendency to split.*—None observed.

*Kernel.*—Shape: Oval. Width: 9 mm average. Length: 16 mm average. Flavor: Bitter (amygdalin is abundant). Color: Light brown, Buckskin (Pantone 16-1342) with darker brown stripes, Topaz (Pantone 16-1150) when first removed from fully ripe, fresh fruit. Viability: Germinates best with embryo culture.

Use: Fresh; Dessert.

Resistance to disease: High resistance to bacterial spot incited by *Xanthomonas campestris* pv. *pruni*. Resistance to other fruit and tree diseases are within the range for commercial peach cultivars in Florida. No unusual resistance or susceptibility or insects and diseases noted.

Keeping quality: Excellent after 2 weeks at 7° C. and with minimal bruises or scarring appearing on skin.

Shipping quality: Degree of firmness at harvest and firmness retained in refrigeration for 2 weeks at 7° C. with no internal breakdown of flesh or appreciable loss of eating quality indicates fruit should be highly acceptable for shipping.

What is claimed is:

1. A new and distinct cultivar of peach tree as illustrated and described herein.

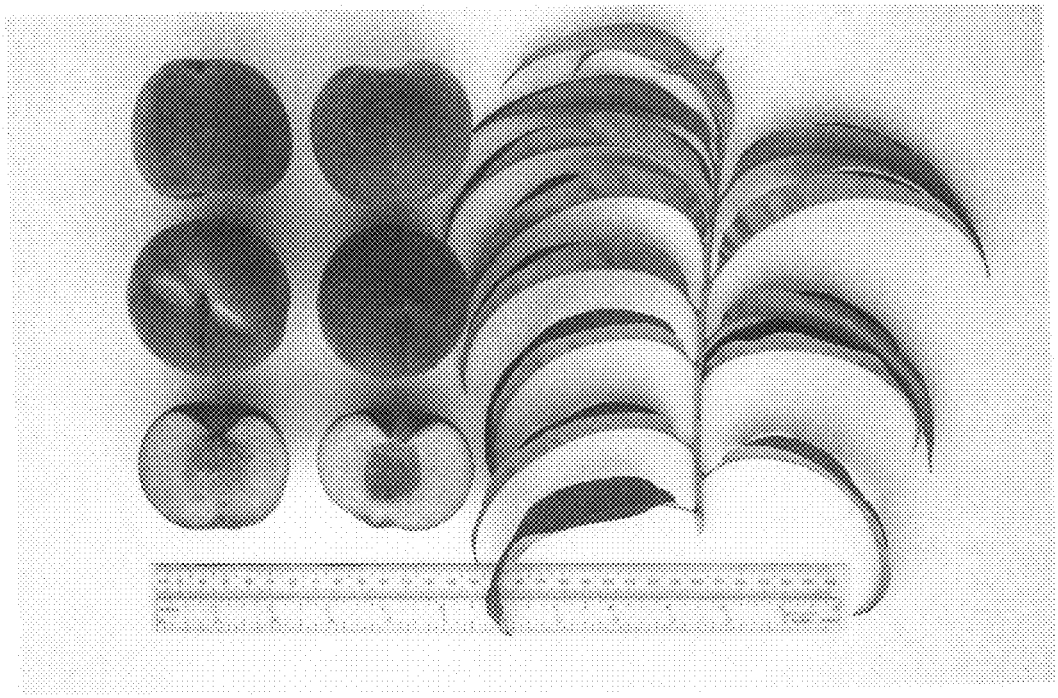

* * * * *